United States Patent
Mussig et al.

(10) Patent No.: US 7,532,929 B2
(45) Date of Patent: May 12, 2009

(54) ADAPTIVE VENTRICULAR RATE SMOOTHING DURING ATRIAL FIBRILLATION

(75) Inventors: Dirk Mussig, West Linn, OR (US); Volker Lang, West Linn, OR (US); Jie Lian, Beaverton, OR (US)

(73) Assignee: Biotronik CRM Patent AG (DE)

( * ) Notice: Subject to any disclaimer, the term of this patent is extended or adjusted under 35 U.S.C. 154(b) by 711 days.

(21) Appl. No.: 11/063,240

(22) Filed: Feb. 22, 2005

(65) Prior Publication Data
US 2005/0187585 A1 Aug. 25, 2005

Related U.S. Application Data

(60) Provisional application No. 60/546,897, filed on Feb. 23, 2004.

(51) Int. Cl.
*A61N 1/08* (2006.01)
(52) U.S. Cl. ............... 607/14; 607/9; 607/25; 607/4; 607/15
(58) Field of Classification Search .......... 607/9, 607/25, 4, 14, 15
See application file for complete search history.

(56) References Cited

U.S. PATENT DOCUMENTS

| | | | |
|---|---|---|---|
| 5,480,413 A | 1/1996 | Greenhut et al. | |
| 5,609,613 A | 3/1997 | Woodson et al. | |
| 5,792,193 A | 8/1998 | Stoop | |
| 5,893,882 A | 4/1999 | Peterson et al. | |
| 6,434,424 B1 | 8/2002 | Igel et al. | |
| 6,501,988 B2 * | 12/2002 | Kramer et al. | 607/9 |
| 6,708,062 B2 * | 3/2004 | Ericksen et al. | 607/9 |

FOREIGN PATENT DOCUMENTS

| | | |
|---|---|---|
| WO | WO 93/14816 | 8/1993 |
| WO | WO 96/15828 | 5/1996 |

* cited by examiner

*Primary Examiner*—Carl H Layno
*Assistant Examiner*—Natasha N Patel
(74) *Attorney, Agent, or Firm*—Hahn Loeser & Parks LLP

(57) ABSTRACT

An implantable cardiac device is provided for adaptive ventricular rate smoothing during atrial fibrillation (AF). When AF is detected, the operation of the device is switched to non-atrial synchronized pacing mode such as DDI, DDIR, VDI, VDIR, VVI, or VVIR. The ventricular escape interval (VEI) is beat-by-beat modulated around a physiological interval zone (PIZ), which is determined by the pre-arrhythmia ventricular rate or the output of rate responsive sensor. The VEI remains unchanged if the preceding ventricular event is sensed and its RR interval is within the PIZ. Otherwise, the VEI is decreased asymptotically toward a lower interval threshold if the preceding RR interval is longer than the upper limit of the PIZ, or the VEI is increased asymptotically toward an upper interval threshold if the preceding RR interval is shorter than the upper limit of the PIZ. The step of incrementing or decrementing the VEI is adaptive to the absolute difference value between the preceding RR interval and the asymptotic interval threshold to ensure fast recovery of deviant RR interval toward the PIZ and to reduce the amount of high rate ventricular paces after a ventricular sense with very short coupling interval.

22 Claims, 4 Drawing Sheets

ADAPTIVE VENTRICULAR RATE SMOOTHING DURING ATRIAL FIBRILLATION

CROSS-REFERENCE TO RELATED APPLICATIONS/INCORPORATION BY REFERENCE

This application claims priority to U.S. provisional patent application Ser. No. 60/546,897, filed on Feb. 23, 2004, which is incorporated herein by reference in its entirety.

TECHNICAL FIELD

Certain embodiments of the present invention relate to implantable medical devices, including pacemakers, defibrillators and cardioverters, which stimulate cardiac tissue electrically to control a patient's heart rhythm. More particularly, certain embodiments of the present invention relate to implantable cardiac devices with a mode switching feature adapted to smooth ventricular rate during atrial fibrillation (AF).

BACKGROUND OF THE INVENTION

An implantable medical device has a housing containing an atrial and a ventricular sensing stage, a ventricular stimulation pulse generator, a ventricular pacing pulse timer, an atrial tachycardia/fibrillation detector, and a rate determination stage.

The ventricular stimulation pulse generator serves for generation of pacing pulses which can be delivered to a ventricle of a patient's heart via an intracardiac pacing lead connected to the ventricular stimulation pulse generator. To connect such an intracardiac lead to the implantable medical device and to the ventricular stimulation pulse generator generally, a connector in a header of the implantable medical device is provided. The header is part of the hermetically tight housing of the implantable medical device.

Timing of the delivery of pacing pulses is crucial. A wrongly timed pacing pulse can provoke a lethal ventricular fibrillation. This may occur if the pacing pulse is timed to fall into a vulnerable phase of the heart occurring at the end of ventricular repolarization.

A ventriclular depolarisation that is a depolarization of myocardial tissue cells of the ventricle cause a ventricular contraction which is felt as a heart beat. Repolarization leads to a relaxation of the myocardial cells and the expansion of the ventricle. Ventriclular depolarisation causes electrical potentials which can be sensed. A sensed ventricular depolarisation is called a sensed ventricular event indicating a ventricular contraction.

Likewise atrial contractions can be detected by sensing electrical potentials in an atrium of the heart.

Delivery of super-threshold electrical pulses to the myocard, herein referred to pacing pulses, causes a depolarisation of the myocard and thereby a contraction of the heart chamber, e.g. ventricle or atrium, the pacing pulse is delivered to.

Generally, it is a purpose of an implantable medical device such as a pacemaker or defibrillator to treat a malfunctioning heart by delivery of timed pacing pulses or defibrillation shocks to ensure a physiologically adequate pacing rate or to terminate a potentially life threatening fibrillation, respectively.

To determine such a physiologically adequate pacing rate, the rate determination stage is provided. In a common rate adaptive pacemaker, the rate determination stage is connected to a physiological sensor to determine the hemodynamic demand of a patient and to adjust the pacing rate accordingly.

Connected to the rate determination stage is a ventricular pacing pulse timer which triggers a ventricular stimulation pulse generator to deliver a ventricular stimulation pulse at the expiration of a ventricular escape interval (VEI) unless a natural (intrinsic) ventricular contraction is sensed prior to expiration of the VEI. Sensing of a ventricular contraction Vs prior to expiration inhibits the delivery of a scheduled ventricular pace Vp.

The duration of the ventricular escape interval depends on the mode of operation of the pacemaker and on the pacing which, in a rate responsive pacemaker, is determined by evaluating hemodynamic demand specific signal from the physiological sensor.

When a heart is stimulated with a desired pacing rate in an atrium synchronous (atrial synchronized) pacing mode like the DDD-mode, the ventricular escape interval is triggered by an atrial event such as a sensed natural atrial contraction (As) or an atrial pace (Ap, atrial pacing pulse). In a dual chamber pacemaker, a scheduled atrial pacing pulse is delivered if no atrial contraction is sensed prior to the scheduled time of atrial pace delivery.

During atrial tachycardia or atrial fibrillation, the natural intrinsic atrial rate generally would lead to too high a ventricular rate in an atrial synchronized pacing mode. In such case, mode-switching is provided to change the pacing mode to a non-synchronous mode like DDI or VVI. If the pacemaker is operated in a non-synchronous mode of pacing, the VEI usually is triggered by a ventricular event. Since the VEI schedules a ventricular pace which will be triggered if the VEI expires without sensing a ventricular event, in the non-synchronous pacing mode the VEI is the reciprocal value of the stimulation rate.

Regarding this description, the terms "atrial synchronized mode" and "atrium synchronous mode" are used synonymously. Likewise, the terms VV-interval and RR-interval are used synonymously to designate the time interval between consecutive ventricular contractions (sensed as R-waves), the time interval being the reciprocal value of the heart rate.

Atrial fibrillation (AF) represents the most common sustained cardiac arrhythmia in clinical practice, and is associated with increased morbidity and mortality (Kannel et al., 1982; Feinberg et al., 1995). In the absence of advanced or complete heart block, the ventricular rhythm during AF is usually irregular and random. Converging evidence suggested that irregular ventricular rhythm during AF contributes significantly to the symptoms and hemodynamic deterioration that are independent of rapid heart rate (Naito et al., 1983; Daoud et al., 1996; Clark et al., 1997). Recent study further suggested that irregular rather than rapid ventricular response during AF might be responsible for the increased risk of recurrent ventricular arrhythmias in ICD recipients (Gronefeld et al., 2000). In addition, irregular ventricular response during AF may significantly increase the sympathetic nerve activity, which is detrimental in patients with congestive heart failure (Wasmund et al., 2003). Antiarrhythmic drugs have been the mainstay of therapy for the management of patients with AF (Prystowsky et al., 1996). However, drug therapy is often unsatisfactory due to limited efficacy (Pacifico et al., 1999), ventricular proarrhythmia (Prystowsky, 1996), and other undesirable side effects.

Various ventricular pacing protocols have been proposed for ventricular rate smoothing (VRS) and to avoid irreversible AV nodal ablation. Wittkampf et al. (1986; 1988) proposed a VVI pacing algorithm in which the ventricular escape interval (VEI) was increased after each paced beat and was decreased after each sensed beat. This method intended to overdrive spontaneous ventricular event and resulted in more than 93% ventricular pacing. Lau et al. (1990) proposed another pacing protocol in which a ventricular pace was delivered after each sensed R wave. However, the method may result in very high ventricular rate and has potential proarrhythmic effect.

U.S. Pat. No. 5,480,413 issued to Greenhut et al. disclosed a VRS algorithm in which the VEI is dynamically adjusted based on the irregularity measurement of the previous RR intervals. This method cannot prevent sudden ventricular pause after trains of short and regular RR intervals. In addition, regularity control without considering trend of RR intervals may result in undesired high rate or low rate. For instance, gradual but regular increase of RR intervals will lead to further decrease of pacing rate, whereas gradual but irregular decrease of RR intervals will lead to further increase of pacing rate.

U.S. Pat. No. 5,792,193 issued to Stoop disclosed a VRS algorithm in which the VEI is determined according to a flywheel rate which is incremented after a ventricular sense and is decremented after a ventricular pace. The flywheel rate tracks the average ventricular rate, and prevents sudden increase of RR interval. However, depending on the parameter settings of increment and decrement, this method may result in inappropriately fast rate (see U.S. Pat. No. 6,434,424), which may increase the risk of pacing-induced heart failure (Simpson et al., 2001).

U.S. Pat. No. 5,893,882 issued to Peterson et al. disclosed a VRS algorithm in which the VEI is modulated based upon preceding RR interval such that the VEI is set equal to the preceding intrinsic or paced interval, with an increment if the preceding interval is less than the preset target interval, or with a decrement if the preceding interval is greater than the target interval. The performance of this algorithm relies on properness of the target interval setting. In addition, the slope of VEI increment or decrement is fixed, independent of the preceding RR interval and the target interval.

U.S. Pat. No. 6,434,424 issued to Igel et al. disclosed a VRS algorithm in which the VEI is continuously modulated by preceding ventricular event sequence, the stability of the intrinsic ventricular rate, and any atrial pace events. This approach results in greater than 50% of ventricular pacing regardless the rate or regularity of the otherwise intrinsic ventricular rhythm. The increment or decrement of VEI is also fixed, independent of the ventricular rate, regularity, and the event sequence.

U.S. Pat. No. 6,501,988 issued to Kramer et al. disclosed a VRS protocol that allows biventricular sensing in order to avoid fusing beat especially when left ventricle is paced. After a ventricular sense, the VEI moves toward the present RR interval multiplied by a scaling factor at a rate determined by a weighting coefficient. After a ventricular pace, the VEI is increased in an exponential manner up to the basic interval. Such a protocol may result in consecutively high rate ventricular pacing after sensed ventricular event with very short RR interval.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention comprises an implantable medical device comprising a PIZ determination stage for determining a physiological interval zone (PIZ) which determines a range of appropriate ventricular escape interval (VEI) duration values for VEI determination, and which is defined by an upper limit (ULPIZ) and a lower limit (LLPIZ). The upper limit defines a longest VV-interval of the physiological interval zone. The lower limit defines a shortest VV-interval of the physiological interval zone. The physiological interval zone extends between the upper limit and the lower limit.

In order to detect an atrial fibrillation (AF), an AF-detector is provided that triggers a mode switching stage. In an embodiment described herein, the AF-detector is connected to an atrial sensing stage in order to evaluate the rate of sensed atrial events. Events sensed in the atrium do not always originate from an atrial contraction. It is possible that a far-field signal of a ventricular event is sensed in the atrium shortly after a ventricular contraction occurs. In order to not incorrectly treat such a far-field signal originating from the ventricle as an atrial contraction, an atrial blanking interval may be triggered by each ventricular event. The concept of atrial blanking after ventricular contraction as such is well known in the art and is of particular benefit when implemented together with embodiments of the present invention.

Alternatively, the AF detector can be connected to the ventricular sensing stage and be adapted to neglect those sensed atrial events from further evaluation which occur in a predetermined time interval after ventricular contraction.

An embodiment of the present invention provides a means for an implantable cardiac device to smooth the ventricular rate during AF, and thus improve a patient's symptom and hemodynamic responses.

An embodiment of the present invention avoids unnecessary high rate pacing, and thus minimizes the detrimental effects of fast ventricular rate during AF.

An embodiment of the present invention preserves as much intrinsic ventricular events as possible if these sensed events are in regular rhythm and the resulting RR intervals are within physiological normal range.

An embodiment of the present invention provides a means of VRS with adaptive features. The beat-to-beat modulation of VEI is adapted to the absolute difference value between the preceding RR interval and the interval thresholds which themselves are also determined adaptively according to the desired physiological interval zone. The modulation of the VEI may also be adapted to the regularity of the RR intervals and the ventricular event sequence.

As a result, an embodiment of the present invention provides implantable cardiac devices having a VRS algorithm that can effectively suppress the irregular ventricular response during AF with limited percentage of ventricular paces, and without compromise on the ventricular rate control.

An embodiment of the present invention is directed to implantable cardiac devices with a mode switching feature adapted to smooth ventricular rate during AF. In a embodiment of the present invention, the device nominally operates in an atrial synchronized pacing mode such as DDD, DDDR, VDD, or VDDR. In response to detection of atrial rhythm characteristics consistent with AF, the device switches into a non-atrial synchronized pacing mode such as DDI, DDIR, VDI, VDIR, VVI, or VVIR. Such mode-switching is generally known in the art.

In the DDI, DDIR, VDI, VDIR, VVI, or VVIR mode, the ventricular pacing rate is determined by the VEI. Since ventricular pacing during mode switching is carried out in an inhibited pacing mode (as indicated by the third letter of the mode code, e.g. DDI. "I" stands for inhibited pacing mode), any ventricular sense (Vs) occurring before the time out of VEI inhibits the ventricular pace (Vp). Otherwise, a Vp is delivered at the expiration of the VEI.

According to an embodiment of the present invention, the VEI is beat-by-beat modulated toward a physiological interval zone (PIZ) which is illustrated in more detail further below.

One aspect of an embodiment of the present invention, which may be realized independent of the feature relating to the determination of an actual VEI, is the aspect of the timing and delivery or inhibition of atrial paces during non-atrial synchronized pacing modes like DDI or DDIR and the implantable medical device is adapted to behave as follows:

If the device operates in DDI or DDIR mode, the device tracks the most recent atrial sense (As). An atrial pace (Ap) is scheduled at a time ($T_{Ap}$) prior to the expiration of VEI, and the time interval between scheduled Ap and Vp is a predefined AV delay (e.g., 150 ms):

$$T_{Ap} = T_v + VEI - AV$$

wherein $T_v$ is the time of occurrence of the latest ventricular event, either a ventricular pace (Vp) or a ventricular sense (Vs).

The Ap will be actually delivered if the interval between the most recent As and the scheduled Ap is longer than a predefined minimum AsAp interval (e.g., 300 ms), otherwise the scheduled Ap is inhibited by the most recent As to avoid competitive atrial pacing.

An atrial pace is inhibited, if:

$$T_{Ap} - T_{As} < AsAp_{min}$$

$T_{Ap} - T_{As}$ is the interval between the latest atrial sense and the time, the next atrial pace is scheduled (see above).

If $T_{Ap} - T_{As}$ is longer or equal $AsAp_{min}$, an atrial pace is delivered at $T_{Ap}$.

Now the aspect of how the VEI during non-atrial synchronized ventricular pacing shall be further illustrated.

As already mentioned, according to one aspect of the invention, the VEI is beat-by-beat modulated toward a physiological interval zone (PIZ).

The PIZ represents the range of ventricular interval that would be considered physiologically normal for the patient. The PIZ can be determined from the segment of RR intervals prior to the AF episode by different methods.

One of the feasible approaches is to calculate the mean ($\mu$) and standard deviation ($\sigma$) of the RR intervals prior to the AF episode, and the PIZ spans from $\mu - k_1 \cdot \sigma$ to $\mu + k_2 \cdot \sigma$, where $k_1$ and $k_2$ are scaling factors where, in accordance with an embodiment of the present invention, both are set to 2. The mean ($\mu$) of the RR intervals prior to the AF episode is the reciprocal value of the mean heart rate prior to the AF episode.

Alternatively, the PIZ can also be determined by setting upper and lower boundaries around the desired ventricular interval determined by the rate responsive sensor if it is available. The rate responsive sensor may be any sensor capable of determining a value indicative to a hemodynamic demand of a patient as known in the art. In the claims, a hemodynamic adequate heart rate as determined by the rate responsive sensor is also referred to as "mean heart rate". The upper limit and the lower limit of the PIZ must be constrained between the predefined pacing basic interval and the upper tracking interval.

If a ventricular sense (sensed ventricular event) is associated with a preceding RR interval (interval between the preceding ventricular event and the ventricular sense), the RR interval falling into the PIZ, no adaptation of the VEI is performed and the last VEI is maintained.

Otherwise, an adaptation of VEI (increase or decrease) is performed by the implantable medical device. To calculate the increase or decrease, the implantable medical device is adapted to refer to the PIZ and to a lower interval threshold (LIT) defining a shortest possible VEI and to an upper interval threshold (UIT) defining a longest possible VEI.

Both, the LIT and the UIT, may be fixed, for example programmed, or may be adaptable by the implantable medical device itself.

The implantable medical device additionally incorporates a basic interval (BI), defining an basic (minimum) pacing rate, of e.g. 60 bpm corresponding to a BI of 1000 ms.

In accordance with an embodiment of the present invention, the LIT lies between the lower limit and the upper limit of the PIZ.

In accordance with an embodiment of the present invention, the UIT lies between the upper limit of the PIZ and the pacing basic interval.

If the preceding RR interval is longer than the upper limit of the PIZ, the VEI is decreased asymptotically toward the lower interval threshold (LIT).

If the preceding RR interval is shorter than the lower limit of the PIZ, the VEI is increased asymptotically toward an upper interval threshold (UIT).

If the preceding RR interval is within the PIZ, the VEI is also increased asymptotically toward the UIT if the preceding ventricular event is paced, or remains unchanged if the preceding ventricular event is sensed.

By this means, not only the irregular ventricular responses during AF are suppressed, but also the intrinsic ventricular depolarizations that are in physiologically normal rate and rhythm are allowed to occur. The preserve of these sensed ventricular events has potentially beneficial effects because it encourages ventricular depolarizations through natural conduction pathway, avoid ventricular pacing induced mitral regurgitation, excitation sequence alteration, and associated adverse effects on myocardial structure and hemodynamics. In addition, a certain degree of heart rate variability within normal range is also preserved.

In accordance with an embodiment of the present invention, the step of incrementing or decrementing VEI is adaptive to the absolute difference value between the preceding RR interval and the asymptotic interval threshold being the LIT or the UIT, respectively. In other words, a greater increment/decrement is made if the difference is larger, while a lesser increment/decrement is made if the difference is smaller. By this means, any deviated ventricular interval recovers fast toward the PIZ while the speed of convergence gradually slows down when the RR interval approaches the target threshold. Compared with other VEI adjustment methods, such as fixed or exponential VEI increment/decrement, this adaptive feature may effectively reduce the amount of high rate pacing after a ventricular sense with very short coupling interval, without compromise of the regularity control.

These and other advantages and novel features of the present invention, as well as details of illustrated embodiments thereof, will be more fully understood from the following description and drawings.

DETAILED DESCRIPTION OF THE INVENTION

An embodiment of the present invention comprises an implantable medical device such as, for example, a pacemaker, or a cardioverter/defibrillator. The implantable medical devices includes a housing which contains an atrial and a ventricular sensing stage, a ventricular stimulation pulse generator, a ventricular pacing pulse timer, an atrial tachycardia/fibrillation detector, a ventricular rate determination stage, and a mode switching stage.

The sensing stages and the stimulation pulse generator are at least indirectly connected to a lead-connector (in a header) for an intracardiac sensing/pacing lead to receive electrical signals from the atrium and the ventricle of a heart and to deliver pacing pulses to the ventricle of the heart. The atrial sensing stage is further connected to the atrial tachycardia/fibrillation detector (ventricular sensing stage may as well be connected to A-tach/Fib Detector in order to eliminate far-field senses of ventricular events in the atrium).

The ventricular pacing pulse timer is connected to the ventricular sensing stage, to the ventricular stimulation pulse generator, and to the ventricular rate determination stage. The ventricular pacing pulse timer is adapted to trigger the ventricular stimulation pulse generator to deliver a ventricular stimulation pulse upon time out of a ventricular escape interval (VEI) and to inhibit the delivery of a ventricular pacing pulse if a ventricular event is sensed by the ventricular sensing stage prior to time-out of the ventricular escape interval.

The ventricular rate determination stage is adapted to generate an appropriate ventricular escape interval duration value. The mode switching stage is connected to the atrial tachycardia/fibrillation detector and to the ventricular pacing pulse timer to switch the pacing mode from an atrium-synchronous mode to a non-synchronous mode upon detection of an atrial tachycardia or an atrial fibrillation or both.

The implantable medical device includes a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein the upper limit defines a longest VV-interval of the physiological interval zone, and wherein the lower limit defines a shortest VV-interval of the physiological interval zone, and wherein the physiological interval zone extends between the upper limit and the lower limit.

Figure 1:
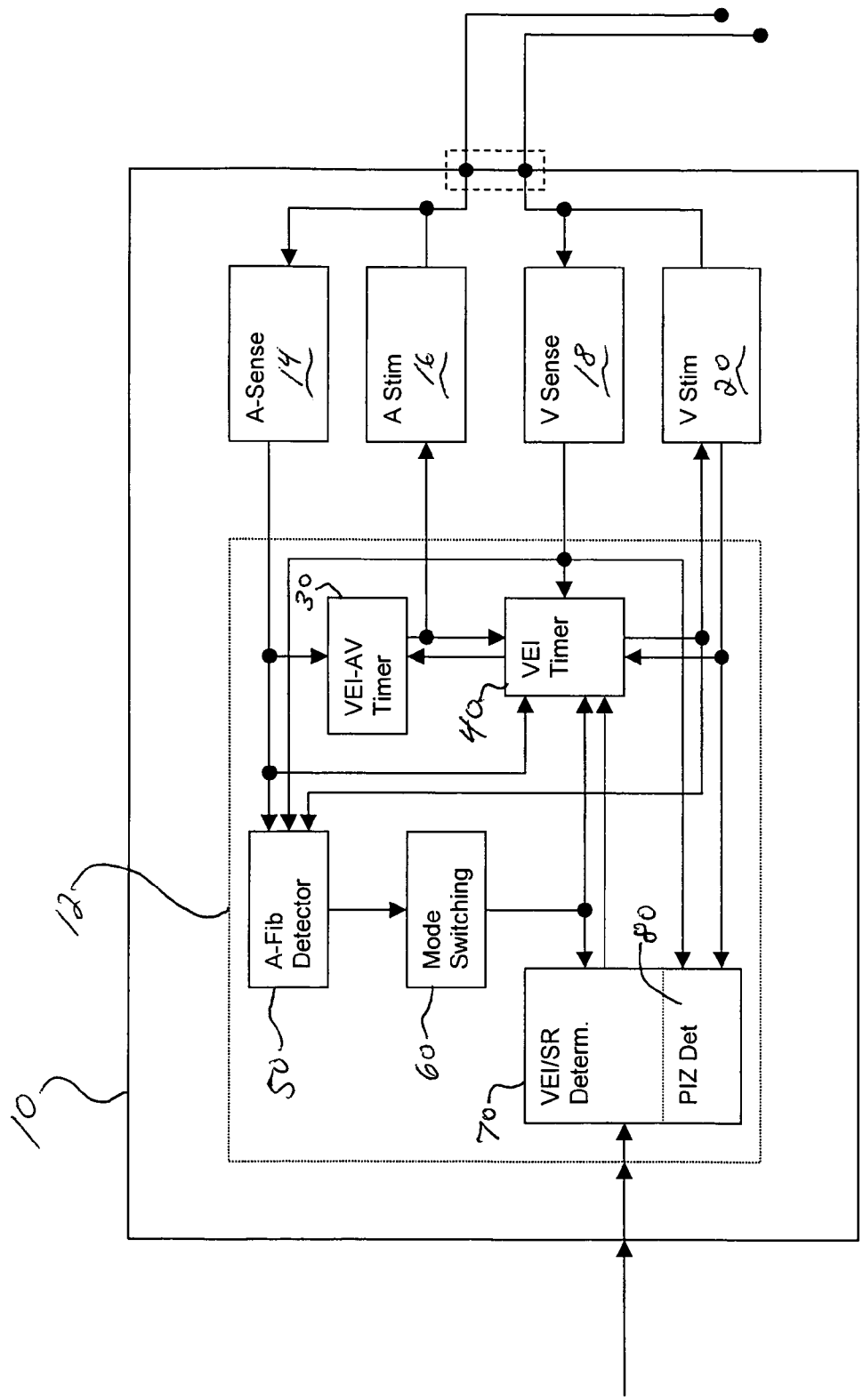
FIG. 1 illustrates a schematic block diagram of an embodiment of an implantable medical device, in accordance with various aspects of the present invention.

Referring to FIG. 1, FIG. 1 shows an implantable pacemaker/defibrillator according to an embodiment of the present invention by a way of a simplified block diagram. In a housing 10, a control unit 12, an atrial sensing stage 14, an atrial stimulation stage 16, a ventricular sensing stage 18 and a ventricular stimulation stage 20 are contained. The atrial stimulation stage 16 and the ventricular stimulation stage 20 both include a stimulation pulse generator.

The housing 10 is hermetically tight and has a connector 22 attached to the housing to which an atrial pacing/sensing lead 24 and a ventricular pacing/sensing lead 26 are connected. By way of the connector 22, the atrial pacing/sensing lead 24 is connected to both, the atrial sensing stage 14 and the atrial stimulation stage 16. Likewise, the ventricular pacing/sensing lead 26 is connected to the ventricular sensing stage 18 and the ventricular stimulation stage 20 via the connector 22.

Both, the atrial stimulation stage 16 and the ventricular stimulation stage 20 are designed to deliver a pacing pulse to the respective lead if triggered.

Triggering of the atrial stimulation stage 16 and/or the ventricular stimulation stage 20 is caused by the control unit 12 and in particular by an atrial timer (VEI-AV timer) 30 and/or a ventricular timer (VEI timer) 40, respectively, being part of the control unit 12 (e.g., as software modules). All elements shown within the control unit 12 may be implemented as software modules, for example, in accordance with an embodiment of the present invention.

The ventricular timer (VEI timer) 40 triggers a ventricular stimulation pulse at the end of a ventricular escape interval (VEI) unless a ventricular contraction is sensed by the ventricular sensing stage 18 prior to expiration of the ventricular escape interval. In the latter case, triggering of the ventricular stimulation pulse is inhibited.

The ventricular escape interval is triggered by an atrial event, for example by a sensed atrial contraction or by an atrial stimulation pulse.

The atrial pacing pulse timer (VEI-AV timer) 30 triggers a scheduled atrial stimulation pulse prior to expiration of the ventricular escape interval, the time difference between the scheduled atrial pace and the expiration of a ventricular escape interval being a predefined AV delay of 150 ms. The atrial stimulation pulse is inhibited, if the time interval between the latest sensed atrial event (As) and the scheduled atrial pace is shorter than 300 ms.

In order to perform a mode switching feature, the control unit 12 comprises an atrial tachycardia/fibrillation detector 50 connected to the atrial sensing stage 14. The atrial tachycardia/fibrillation detector 50 triggers a mode switching stage 60 upon detection of an atrial tachycardia of an atrial fibrillation. The mode switching stage 60 causes the ventricular pacing pulse timer 40 to switch from an atrial synchronized stimulation mode to a non-sychronized stimulation mode.

In order to determine an adequate ventricular escape-interval, a stimulation rate determination stage 70 is provided which calculates a ventricular escape interval (VEI) based on the features described herein in further detail. The stimulation rate determination stage 70 may be connected to a physiological sensor outside the housing 10 of the pacemaker/defibrillator. The stimulation rate determination stage 70 includes a PIZ determination stage 80, whose functionality is described later herein, in accordance with an embodiment of the present invention. Alternatively, the PIZ determination stage 80 may be implemented as a module which is separate from the stimulation rate determination stage 70.

Figure 2:
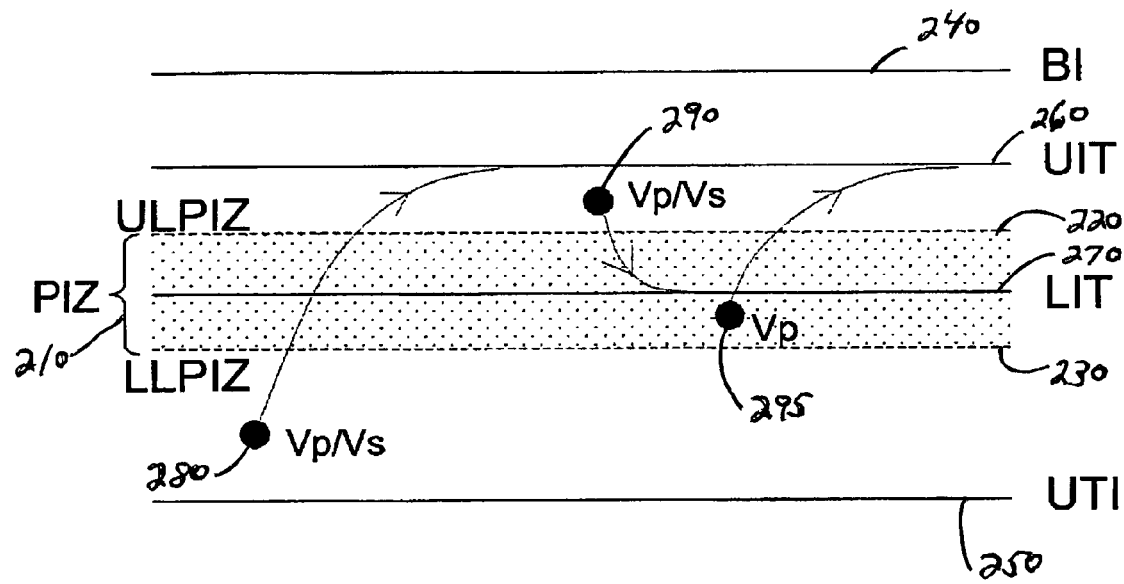
FIG. 2 is a graph illustrating the concept of adaptive VEI modulation according to the settings of physiological interval zone, upper and lower limits of interval threshold, in accordance with an embodiment of the present invention.

FIG. 2 graphically illustrates the operation of the control unit 12 and the concept of adaptive VEI modulation described herein. Detection of an atrial fibrillation (AF) triggers a ventricular rate smoothing (VRS) feature. When the ventricular rate smoothing (VRS) feature is operative after AF detection, a physiological interval zone (PIZ) 210 is determined based on the mean and standard deviation of the RR intervals prior to the AF episode, or based on the desired ventricular interval determined by the rate responsive sensor if it is available. The upper limit of the PIZ (ULPIZ) 220 and the lower limit of the PIZ (LLPIZ) 230 should be bounded by a basic interval (BI) 240 and an upper tracking interval (UTI) 250. Both, basic interval 240 and upper tracking interval 250 are intervals known from prior art pacemakers.

In addition to the ULPIZ 220 and the LLPIZ 230, an upper interval threshold (UIT) 260 and a lower interval threshold (LIT) 270 are adapted to the PIZ 210. The UIT 260 is set between the ULPIZ 220 and the BI 240. For example, UIT 260 can be set as UIT=max(ULPIZ+δ, BI), where δ is a predefined positive interval that can range from tens to hundreds of millisecond. Or UIT 260 can be set as UIT=ULPIZ+$\lambda_1$·(BI−ULPIZ), where 0<$\lambda_2$≦1. The LIT 270 is set below the ULPIZ 220, while preferably not smaller than the LLPIZ 230. For instance, LIT 270 can be set as LIT=LLPIZ+$\lambda_2$·(ULPIZ−LLPIZ), where 0≦$\lambda_2$<1.

The VEI is modulated beat by beat based upon the preceding ventricular event and its interval with respect to the desired PIZ. If the RR interval of the preceding event (either Vp or Vs) is lower than the LLPIZ 230 (marked by the left circle 280 in FIG. 2), the VEI is increased asymptotically toward the UIT 260. If the RR interval of the preceding event (either Vp or Vs) is higher than the ULPIZ 220 (marked by the middle circle 290 in FIG. 1), the VEI is decreased asymptotically toward the LIT 270. If the preceding RR interval is within the PIZ 210 (marked by the right circle 295 in FIG. 1), the VEI is also increased asymptotically toward the UIT 260 if the preceding event is a Vp, or remains unchanged if the preceding event is a Vs.

If VEI adjustment is necessary, its step of increment/decrement is adaptive to the absolute difference value between the preceding RR interval and the asymptotic interval threshold, such that a greater increment/decrement is made if the difference is larger, whereas a lesser increment/decrement is made if the difference is smaller. Dependent upon different conditions, the adjustment of VEI (except for the VEI unchanged case) will follow the according traces as illustrated in FIG. 2 unless the condition is changed or a ventricular sense occurs before the expiration of the VEI. As noted, although the PIZ has an upper boundary of ULPIZ, the present VRS algorithm allows the VEI to transiently exceed the ULPIZ, immediately followed by decrement of VEI toward the LIT due to condition change. This is considered appropriate because the PIZ (determined either by the RR intervals prior to the AF episode or by the rate responsive sensor) is at best only an approximate of the truly desired interval range, and the overshoot of the VEI above the ULPIZ is limited by its asymptotic convergence toward the UIT. In addition, slightly prolonging the VEI above the ULPIZ potentially allows normal intrinsic ventricular depolarization to occur (i.e., RR interval is within PIZ).

Figure 3:
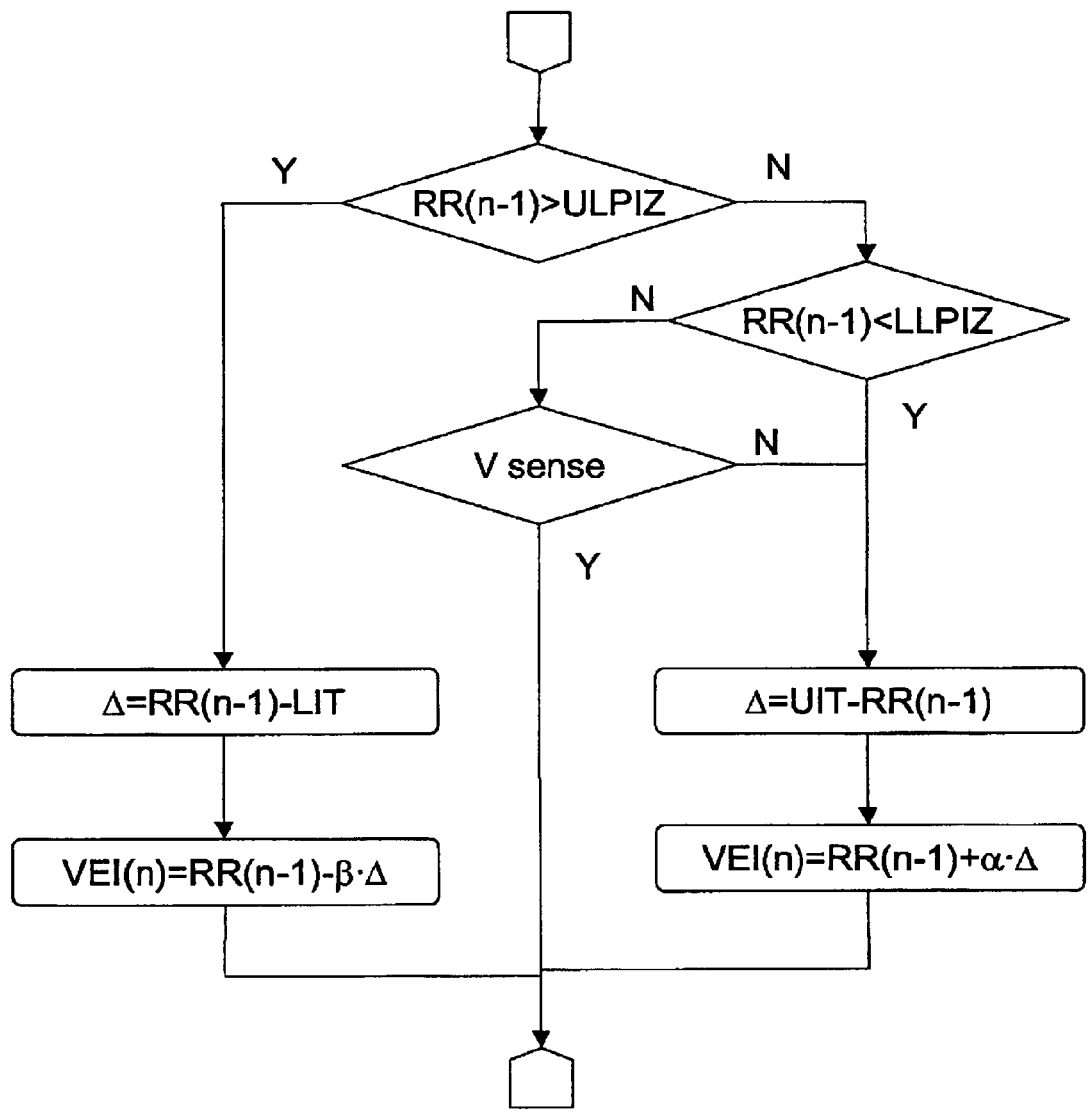
FIG. 3 is a flow chart illustrating the adaptive VRS algorithm during AF, in accordance with an embodiment of the present invention.

In accordance with an embodiment of the present invention, FIG. 3 illustrates the flow chart of the present adaptive VRS algorithm. The ULPIZ, LLPIZ, UIT, and LIT are determined after VF detection according to the previous description herein. After each ventricular event, the algorithm compares its interval, RR(n−1), with the boundaries of the PIZ. If RR(n−1)>ULPIZ, then the difference between RR(n−1) and the LIT is calculated: Δ=RR(n−1)−LIT. The next VEI is then determined as: VEI(n)=RR(n−1)−β·Δ, where 0<β<1. If RR(n−1)<LLPIZ, then the difference between UIT and RR(n−1) is calculated: Δ=UIT−RR(n−1). The next VEI is then determined as: VEI(n)=RR(n−1)+α·Δ, where 0<α<1. In the case of LLPIZ≦RR(n−1)≦ULPIZ, the VEI is either kept unchanged after the Vs, or incremented toward the UIT after the Vp (same as the in case of RR(n−1)<LLPIZ). The parameters α and β control the speed of VEI convergence toward the UIT and LIT, respectively. These parameters can be predefined values, preferably in the range between 0.05 and 0.20. Or optionally, they can be dynamically adjusted based on the regularity of the most recent RR intervals and/or the ventricular event sequence. For example, α may be decremented or incremented to enhance or reduce the regularity of the RR intervals that are shorter than the LLPIZ, and β may be independently adjusted in a similar way to modulate the regularity of the RR intervals that are larger than the ULPIZ. Alternatively, α may be dynamically adjusted based on the relative frequency of Vp and Vs for the most recent ventricular events whose RR intervals are shorter than the LLPIZ, and β may be similarly adjusted based on the recent ventricular event sequence for the RR intervals that are larger than the ULPIZ. In all cases, the dynamic adjustment of α and β should be implemented using certain negative feedback (close-loop control), and must be limited within a predefined range (e.g., between 0.05 and 0.20).

Figure 4:
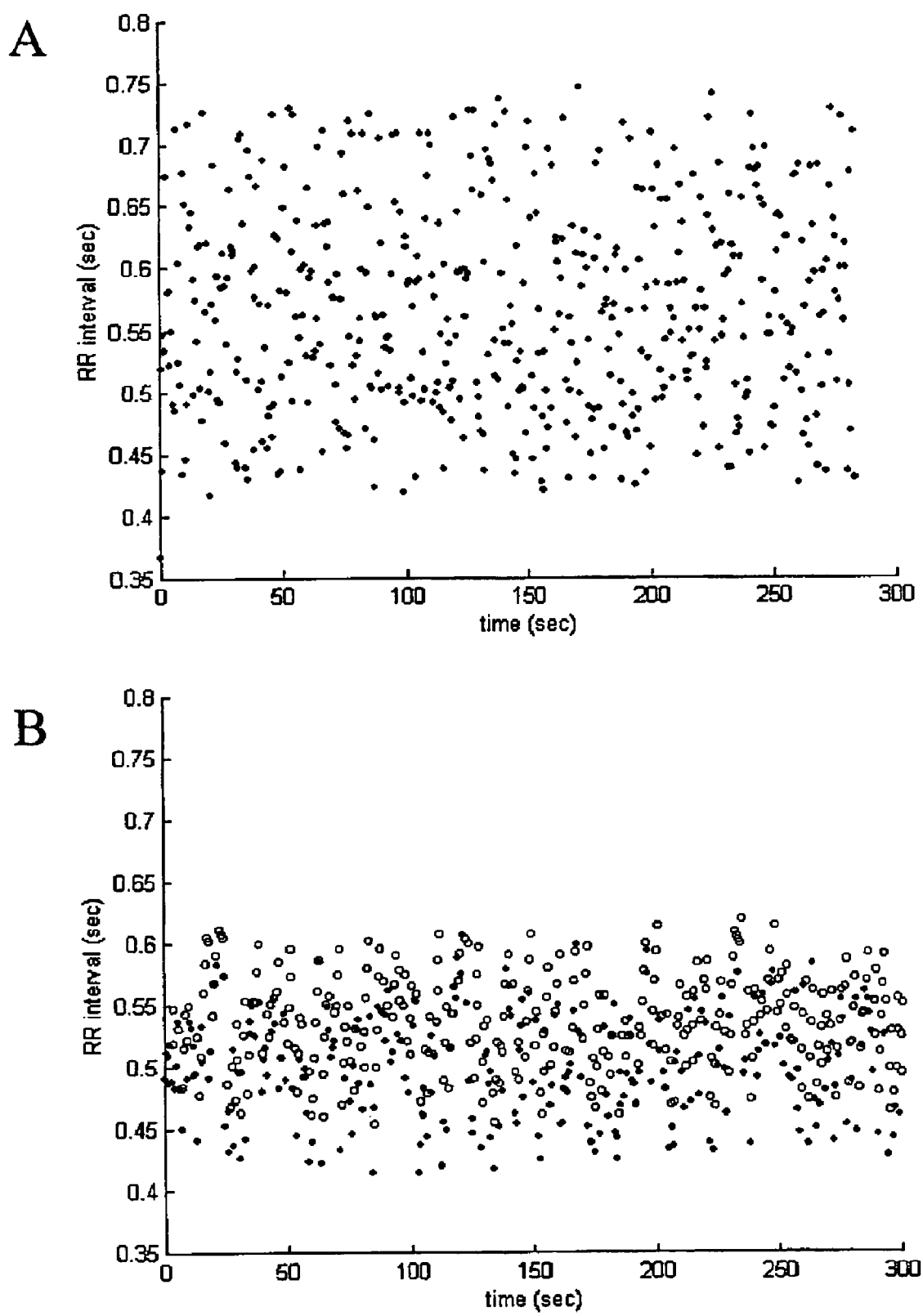
FIG. 4A illustrates an exemplary graph of irregular ventricular interval during AF, in accordance with an embodiment of the present invention.
FIG. 4B illustrates an exemplary graph of the effect of VRS, in accordance with an embodiment of the present invention.

FIGS. 4A-4B show an example to illustrate the effects of the present adaptive VRS when it is operative during an AF episode. FIG. 4A shows a segment of RR intervals during an episode of AF, which is simulated based on the quantitative AF model disclosed by Cohen et al. (1983). As expected, the irregular ventricular response to AF results in large variation of RR intervals. When the adaptive VRS feature is operative (parameter settings: α=0.1, β=0.1, ULPIZ=0.60 sec, LLPIZ=0.55 sec, UIT=0.80 sec, LIT=0.575 sec), the resulting RR intervals are substantially regularized as shown in FIG. 4B. The VRS pacing (open circles) effectively eliminates the very long ventricular pauses and all ventricular paces have RR intervals longer than 0.45 sec. Meanwhile, many ventricular senses (solid dots) within the PIZ (between 0.55 sec and 0.60 sec) are preserved.

According to clinical experience, the ventricular senses with very short coupling intervals are also expected to be suppressed by the VRS pacing in real practice (Wittkampf et al., 1988; Greenhut et al., 1996).

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An implantable medical device, said implantable medical device comprising:
   a housing;
   an atrial sensing stage;
   a ventricular sensing stage;
   a ventricular stimulation pulse generator;
   an atrial stimulation pulse generator;
   a ventricular pacing pulse timer;
   an atrial tachycardia/fibrillation detector;
   a ventricular rate determination stage;
   a mode switching stage, wherein said mode switching stage causes said ventricular pacing pulse timer to switch from an atrial synchronized stimulation mode to a non-synchronized stimulation mode; and
   a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit, and wherein, in an atrium-synchronous mode, a timing of ventricular pacing pulses is determined by an AV-interval triggered by an atrial event associated to an atrial contraction and wherein, in a non-synchronous ventricular pacing mode, said timing of ventricular pacing pulses is determined by said ventricular escape interval determined by a ventricular rate determination stage of said implantable medical device, and wherein the PIZ determination stage is operationally connected to said ventricular rate determination stage and wherein the ventricular rate determination stage is adapted to generate a ventricular escape interval duration value on a beat-to-beat basis for each cardiac cycle based upon a VV-interval duration of a preceding cardiac cycle with respect to the actual physiological interval zone upper and lower limits.

2. The implantable medical device of claim 1, wherein said sensing stages and said stimulation pulse generators are at least indirectly connected to a lead-connector, in a header, for an intracardiac sensing/pacinig lead to receive electrical signals from an atrium and a ventricle of a heart and to deliver pacing pulses to said ventricle of said heart.

3. The implantable medical device of claim 2, wherein said atrial sensing stage is further connected to said atrial tachycardia/fibrillation detector to eliminate far-field senses of ventricular events in said atrium.

4. The implantable medical device of claim 3, wherein said ventricular pacing pulse timer is connected to said ventricular sensing stage, to said ventricular stimulation pulse generator, and to said ventricular rate determination stage.

5. The implantable medical device of claim 4, wherein said ventricular pacing pulse timer is adapted to:
trigger said ventricular stimulation pulse generator to deliver a ventricular stimulation pulse upon time out of a ventricular escape interval (VEI); and
inhibit a delivery of a ventricular pacing pulse if a ventricular event is sensed by said ventricular sensing stage prior to time out of said ventricular escape interval.

6. The implantable medical device of claim 5, wherein said ventricular rate determination stage is adapted to generate an appropriate ventricular escape interval (VEI) duration value.

7. The implantable medical device of claim 6, wherein said mode switching stage is connected to said atrial tachycardia/fibrillation detector and to said ventricular pacing pulse timer to switch a pacing mode from an atrium-synchronous mode to a non-synchronous mode upon detection of an atrial tachycardia or atrial fibrillation or both.

8. An implantable medical device, said implantable medical device comprising:
a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit,
wherein the PIZ determination stage is adapted to determine a physiological interval zone based upon a mean heart rate being the mean heart rate prior to mode switching from an atrium-synchronous mode to an asynchronous mode or a physiologically adequate heart rate determined by a hemodynamic demand sensor (physiologic sensor),
and wherein the PIZ determination stage is adapted to determine the physiological interval zone such that the upper limit defines an RR-interval that is longer by a first difference value d1 than the reciprocal value $\mu$ of the mean heart rate, and the lower limit defines an RR-interval that is shorter by a second difference value $d_2$ than the reciprocal value $\mu$ of the mean heart rate.

9. An implantable medical device, said implantable medical device comprising:
a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VY-interval of the physiological interval zone, and wherein said physiological interval zone extends between said upper limit and said lower limit,
wherein, in an atrium-synchronous mode, a timing of ventricular pacing pulses is determined by an AV-interval triggered by an atrial event associated to an atrial contraction and wherein, in a non-synchronous ventricular pacing mode, said timing of ventricular pacing pulses is determined by said ventricular escape interval determined by a ventricular rate determination stage of said implantable medical device,
wherein the PIZ determination stage is adapted to generate an upper interval threshold (UIT) and a lower interval threshold (LIT), and wherein the ventricular rate determination stage is adapted to generate a ventricular escape interval duration value on a beat-to-beat basis for each cardiac cycle based upon a VV-interval duration of a preceding cardiac cycle with respect to the actual physiological interval zone upper and lower limits and the upper interval threshold (UIT) and the lower interval threshold (LIT),
wherein the ventricular rate determination stage is adapted to determine whether the most recent VV-interval is longer than the upper limit of the physiological interval zone (PIZ) and to decrease the ventricular escape interval toward the lower interval threshold (LIT) if the most recent VV interval is longer than the upper limit of the physiological interval zone (PIZ), and
wherein the ventricular rate determination stage is adapted to decrement the ventricular escape interval asymptotically to the lower interval threshold (LIT) depending on the absolute difference value between the preceding VV-interval and the lower interval threshold.

10. An implantable medical device, said implantable medical device comprising:
a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit,
wherein, in an atrium-synchronous mode, a timing of ventricular pacing pulses is determined by an AV-interval triggered by an atrial event associated to an atrial contraction and wherein, in a non-synchronous ventricular pacing mode, said timing of ventricular pacing pulses is determined by said ventricular escape interval determined by a ventricular rate determination stage of said implantable medical device, and wherein the PIZ determination stage is adapted to generate an upper interval threshold (UIT) and a lower interval threshold (LIT), and wherein the ventricular rate determination stage is adapted to generate a ventricular escape interval duration value on a beat-to-beat basis for each cardiac cycle based upon a VV-interval duration of a preceding cardiac cycle with respect to the actual physiological interval zone upper and lower limits and the upper interval threshold (UIT) and the lower interval threshold (LIT), wherein the ventricular rate determination stage is adapted to determine whether the most recent VV-interval is shorter than the lower limit of the physiological interval zone (PIZ) and to increase the ventricular escape interval toward the upper interval threshold (UIT) if the most recent VV interval is shorter than the lower limit of the physiological interval zone (PIZ), and wherein the ventricular rate determination stage is adapted to increment the ventricular escape interval asymptotically to the upper interval threshold (UIT) depending on an absolute difference value between the preceding VV-interval and the upper interval threshold.

11. An implantable medical device, said implantable medical device comprising:

a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest MV-interval of the physiological interval zone, and wherein said physiological interval zone extends between said upper limit and said lower limit, wherein, in an atrium-synchronous mode, a timing of ventricular pacing pulses is determined by an AV-interval triggered by an atrial event associated to an atrial contraction and wherein, in a non-synchronous ventricular pacing mode, said timing of ventricular pacing pulses is determined by said ventricular escape interval determined by a ventricular rate determination stage of said implantable medical device, wherein the PIZ determination stage is adapted to generate an upper interval threshold (UIT) and a lower interval threshold (LIT), and wherein the ventricular rate determination stage is adapted to generate a ventricular escape interval duration value on a beat-to-beat basis for each cardiac cycle based upon a VV-interval duration of a preceding cardiac cycle with respect to the actual physiological interval zone upper and lower limits and the upper interval threshold (UIT) and the lower interval threshold (LIT), wherein the ventricular rate determination stage is adapted to determine whether the preceding VV-interval is within the physiological interval zone (PIZ) and to increase the ventricular escape interval (VEI) toward the upper interval threshold (UIT) if a preceding ventricular event is paced, and wherein the ventricular rate determination stage is adapted to increment the ventricular escape interval asymptotically to the upper interval threshold (UIT) depending on an absolute difference value between the preceding VV-interval and the upper interval threshold.

12. An implantable medical device, said implantable medical device comprising:

a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit, wherein the PIZ determination stage is adapted to determine a physiological interval zone based upon a mean heart rate being the mean heart rate prior to mode switching from an atrium-synchronous mode to an asynchronous mode or a physiologically adequate heart rate determined by a hemodynamic demand sensor (physiologic sensor), wherein the PIZ determination stage is adapted to determine the physiological interval zone such that the upper limit defines an RR-interval that is longer by a first difference value $d_1$ than the reciprocal value $\mu$ of the mean heart rate, and the lower limit defines an RR-interval that is shorter by a second difference value $d_2$ than the reciprocal value $\mu$ of the mean heart rate, and wherein the first and the second difference values have the same absolute value.

13. An implantable medical device, said implantable medical device comprising:

a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit, wherein the PIZ determination stage is adapted to determine a physiological interval zone based upon a mean heart rate being the mean heart rate prior to mode switching from an atrium-synchronous mode to an asynchronous mode or a physiologically adequate heart rate determined by a hemodynamic demand sensor (physiologic sensor), wherein the PIZ determination stage is adapted to determine the physiological interval zone such that the upper limit defines an RR-interval that is longer by a first difference value $d_1$ than the reciprocal value $\mu$ of the mean heart rate, and the lower limit defines an RR-interval that is shorter by a second difference value $d_2$ than the reciprocal value $\mu$ of the mean heart rate, and wherein the PIZ determination stage is adapted to determine the physiological interval zone such that an absolute value of the first difference value $d_1$ is a product of a standard deviation ($\sigma$) of the VV-intervals prior to mode switching and a first scaling factor $k_1$ 14. The implantable medical device of claim 13, wherein the first scaling factor is set to 2.

15. An implantable medical device, said implantable medical device comprising:

a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit, wherein the PIZ determination stage is adapted to determine a physiological interval zone based upon a mean heart rate being the mean heart rate prior to mode switching from an atrium-synchronous mode to an asynchronous mode or a physiologically adequate heart rate determined by a hemodynamic demand sensor (physiologic sensor), wherein the PIZ determination stage is adapted to determine the physiological interval zone such that the upper limit defines an RR-interval that is longer by a first difference value $d_1$ than the reciprocal value $\mu$ of the mean heart rate, and the lower limit defines an RR-interval that is shorter by a second difference value $d_2$ than the reciprocal value $\mu$ of the mean heart rate, and wherein the PIZ determination stage is adapted to determine the physiological interval zone such that an absolute value of the second difference value $d_2$ is a product of a standard deviation ($\sigma$) of the VV-intervals prior to mode switching and a second scaling factor $k_2$.

16. The implantable medical device of claim 15, wherein the second scaling factor is set to 2.

17. An implantable medical device, said implantable medical device comprising:

a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit, wherein, in an atrium-synchronous mode, a timing of ventricular pacing pulses is determined by an AV-interval triggered by an atrial event associated to an atrial contraction and wherein, in a non-synchronous ventricular pacing mode, said timing of ventricular pacing pulses is determined by said ventricular escape interval determined by a ventricular rate determination stage of said implantable medical device, wherein the PIZ determination stage is adapted to generate an upper interval threshold (UIT) and a lower interval threshold (LIT), and wherein the ventricular rate determination stage is adapted to generate a ventricular escape interval duration value on a beat-to-beat basis for each cardiac cycle based upon a VV-interval duration of a preceding cardiac cycle with respect to the actual physiological interval zone upper and lower limits and the upper interval threshold (UIT) and the lower interval threshold (LIT), and wherein the PIZ determination stage is adapted to generate the upper interval threshold (UIT) such that the upper interval threshold (UIT) is set between the upper limit (ULPIZ) and a basic interval BI.

18. The implantable medical device of claim 17, wherein the PIZ determination stage is adapted to generate the upper interval threshold (UIT) such that the upper interval threshold (UIT) is set equal to the longer interval of the basic interval (BI) and the upper limit plus $\delta$, (ULPIZ+$\delta$), where $\delta$ is a predefined positive interval that can range from tens to hundreds of millisecond.

19. The implantable medical device of claim 17, wherein the PIZ determination stage is adapted to generate the upper interval threshold (UIT) such that the upper interval threshold (UIT) is set equal to the upper limit (ULPIZ) plus $\lambda_1 \cdot$(BI-ULPIZ), where $0<\lambda_1\leq 1$, and where $\lambda_1$ is a weighting factor.

20. An implantable medical device, said implantable medical device comprising:

a PIZ determination stage for determining a physiological interval zone (PIZ) which determines a range of appropriate vetricular escape interval (VEI) duration values for VEI determination, and which is defined by an upper limit (ULPIZ) and a lower limit (LLPIZ), wherein said upper limit defines a longest VV-interval of the physiological interval zone, and wherein said lower limit defines a shortest VV-interval of the physiological interval zone, and wherein said physiological interval zone extends between said upper limit and said lower limit, wherein, in an atrium-synchronous mode, a timing of ventricular pacing pulses is determined by an AV-interval triggered by an atrial event associated to an atrial contraction and wherein, in a non-synchronous ventricular pacing mode, said timing of ventricular pacing pulses is determined by said ventricular escape interval determined by a ventricular rate determination stage of said implantable medical device, wherein the PIZ determination stage is adapted to generate an upper interval threshold (UIT) and a lower interval threshold (LIT), and wherein the ventricular rate determination stage is adapted to generate a ventricular escape interval duration value on a beat-to-beat basis for each cardiac cycle based upon a VV-interval duration of a preceding cardiac cycle with respect to the actual physiological interval zone upper and lower limits and the upper interval threshold (UIT) and the lower interval threshold (LIT), and wherein the PIZ determination stage is adapted to generate the lower interval threshold (LIT) such that the lower interval threshold (LIT) is set below the upper limit (ULPIZ).

21. The implantable medical device of claim 20, wherein the PIZ determination stage is adapted to generate the lower interval threshold (LIT) such that the lower interval threshold (LIT) is set between the upper limit (ULPIZ) and the lower limit (LLPIZ).

22. The implantable medical device of claim 21, wherein the PIZ determination stage is adapted to generate the lower interval threshold (LIT) such that the lower interval threshold (LIT) is set equal to the sum of the lower limit (LLPIZ) plus $\lambda_2 \cdot$(ULPIZ-LLPIZ), where $0\leq\lambda_2<1$, and where $\lambda_2$ is a weighting factor.

* * * * *

UNITED STATES PATENT AND TRADEMARK OFFICE
CERTIFICATE OF CORRECTION

PATENT NO. : 7,532,929 B2 Page 1 of 1
APPLICATION NO. : 11/063240
DATED : May 12, 2009
INVENTOR(S) : Dirk Mussig and West Linn It is certified that error appears in the above-identified patent and that said Letters Patent is hereby corrected as shown below:

Col. 12, claim 9, line 20 replace "VY" with --VV--
Col. 13, claim 11, line 38 replace "MV" with --VV--
Col. 14, claim 13, line 42 replace "1imit" with --limit--

Signed and Sealed this

Fourteenth Day of July, 2009

JOHN DOLL
*Acting Director of the United States Patent and Trademark Office*